US008357024B2

(12) United States Patent  (10) Patent No.: US 8,357,024 B2
Baker-Jackson  (45) Date of Patent: Jan. 22, 2013

(54) STRETCHABLE BAND AND ADJUSTABLE STRAP ATTACHMENT FOR BREASTFEEDING

(76) Inventor: Charla Baker-Jackson, Los Angeles, CA (US)

( * ) Notice: Subject to any disclaimer, the term of this patent is extended or adjusted under 35 U.S.C. 154(b) by 0 days.

(21) Appl. No.: 13/016,717

(22) Filed: Jan. 28, 2011

(65) Prior Publication Data

US 2011/0184344 A1    Jul. 28, 2011

Related U.S. Application Data

(60) Provisional application No. 61/299,235, filed on Jan. 28, 2010.

(51) Int. Cl.
*A41C 1/06* (2006.01)
(52) U.S. Cl. ......................................................... 450/18
(58) Field of Classification Search .................. 601/166; 450/47, 18, 62–64; 604/73, 74, 77–79
See application file for complete search history.

(56) References Cited

U.S. PATENT DOCUMENTS

| | | | | |
|---|---|---|---|---|
| 3,054,408 | A * | 9/1962 | Cousins | 450/60 |
| 3,710,800 | A * | 1/1973 | Carey | 450/64 |
| 5,024,628 | A * | 6/1991 | Sanchez | 450/36 |
| 5,459,903 | A * | 10/1995 | Treacy | 24/3.13 |
| 5,697,830 | A * | 12/1997 | White | 450/36 |
| 6,004,186 | A * | 12/1999 | Penny | 450/36 |
| 6,227,936 | B1 * | 5/2001 | Mendoza | 450/36 |
| 6,237,599 | B1 * | 5/2001 | Maulding | 128/845 |
| 6,346,027 | B1 * | 2/2002 | Merkovsky | 450/37 |
| 6,427,244 | B1 * | 8/2002 | Speier et al. | 2/104 |
| 6,540,702 | B1 * | 4/2003 | Sarango | 601/133 |
| 6,761,614 | B2 * | 7/2004 | Pinna | 450/81 |
| 6,764,377 | B2 * | 7/2004 | Gillan | 450/36 |
| 6,855,029 | B2 * | 2/2005 | Rothman | 450/36 |
| 6,866,558 | B2 * | 3/2005 | Luciano et al. | 450/36 |
| D555,897 | S * | 11/2007 | Pietraroia | D3/229 |
| 7,435,155 | B2 * | 10/2008 | Reinisch et al. | 450/59 |
| 7,470,168 | B1 * | 12/2008 | Farrell | 450/47 |
| 7,540,049 | B2 * | 6/2009 | Sklenarik et al. | 5/630 |
| 7,611,399 | B2 * | 11/2009 | Brigham | 450/36 |
| 7,950,980 | B2 * | 5/2011 | Solberg et al. | 450/36 |
| 8,016,640 | B2 * | 9/2011 | Morgan | 450/62 |
| 2007/0123143 | A1 * | 5/2007 | Morgan | 450/1 |
| 2009/0094752 | A1 * | 4/2009 | Gagliano et al. | 5/655 |

* cited by examiner

*Primary Examiner* — Christopher D Koharski
*Assistant Examiner* — Diva K Chander
(74) *Attorney, Agent, or Firm* — Sughrue Mion, PLLC

(57) ABSTRACT

A size-adjustable, breastfeeding band that helps to lessen the likelihood of infant suffocation during breastfeeding, comprising a primary band, comprised of elastic (or stretchable material) that securely and comfortably extends around the entire middle portion of the breast and fastens via button, snap, drawstring, Velcro, or any other related material or adhesive that can securely hold band in place; and an adjustable strap attachment co-operable with the primary band by attaching into it and preventing slippage.

17 Claims, 6 Drawing Sheets

PRIMARY BAND with ADJUSTABLE STRAP ATTACHMENT DRAPED OVER NECK

BEFORE & AFTER ILLUSTRATIONS OF BREASTFEEDING WITH/WITHOUT PRIMARY BAND

PRIMARY BAND & ADJUSTABLE STRAP ATTACHMENT
(Drawstring Appendage)

PRIMARY BAND with BUTTON & METAL HOOK BARS

PRIMARY BAND with ADJUSTABLE STRAP
ATTACHMENT DRAPED OVER NECK

PRIMARY BAND with ADJUSTABLE STRAP
ATTACHMENT DRAPED OVER NECK & UNDER ARM

TRANSPORTABLE POUCH with DRAWSTRING

Figure 6 & 7
BEFORE & AFTER ILLUSTRATIONS OF
BREASTFEEDING WITH/WITHOUT PRIMARY BAND
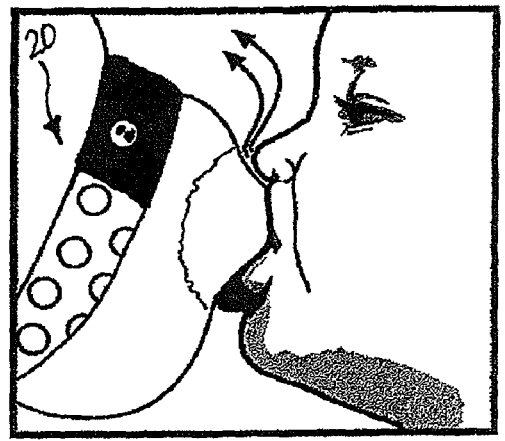
Fig 6    Fig 7

STRETCHABLE BAND AND ADJUSTABLE STRAP ATTACHMENT FOR BREASTFEEDING

CROSS-REFERENCE TO RELATED PATENT APPLICATIONS

This application claims priority from provisional patent application No. 61/299,235, filed on Jan. 28, 2010, in the United States Patent and Trademark Office, the disclosure of which is incorporated herein in its entirety by reference.

BACKGROUND

1. Field

Exemplary embodiments relate to a process and apparatus for safe breastfeeding. More specifically, exemplary embodiments relate to an elastic (or any other stretchable material) primary band, designed to compress the non-areola/non-nipple portion of the breast, and an adjustable strap attachment designed to hold the primary band in place; thus, making breastfeeding safer for the baby by lessening the likelihood of suffocation due to the risk of excess breast tissue smothering and/or compressing against the infant's nose while nursing.

2. Description of the Related Art

Any discussion of the related art throughout the specification should in no way be considered as an admission that such related art is widely known or forms part of common general knowledge in the field.

Breastfeeding has multiple benefits for both the child and the mother. Breast milk contains the essential nutrients and antibodies that build the foundation of a child's lifetime of health. Medical research has shown that breast milk can offer lifelong protection against a variety of potentially life threatening diseases and chronic disorders. Not only does breastfeeding assist in the development of a strong and healthy immune system for the child, but in the era of a harsh economic climate, breastfeeding is a free and cost efficient, natural resource option for feeding a baby. With breastfeeding, food is replenished according to nature's time clock to meet the baby's ongoing and unpredictable feeding demands and patterns. Breastfeeding can also positively impact a woman's health following childbirth by aiding in the mother's weight loss by contracting the stomach muscles as a direct result of the baby's suckling motions. Weight loss is key in restoring a woman's body and health by reducing fat and burning calories.

Breastfeeding is not without its challenges, particularly in the early stages following delivery when the flow of milk is not fully maximized. For example, pain can occur when the breasts become engorged. Another challenge is the feeding position. Whether cradling the baby in one arm, or lying down beside the baby during a feeding, breastfeeding mothers almost always have to use one hand to hold the baby, and the other to hold the breast in proper place throughout a feeding, so that it does not press against a child's petite and fragile nose. This is especially a major issue for women with large breasts who want all of the above mentioned benefits of breastfeeding, but fear the possible life threatening repercussions that can result if the breast tissue covers the child's nose, particularly if the mother is unaware. For instance, it is not uncommon due to the lactation induced hormonal changes for a mother to become extremely drowsy while nursing. There have been instances in history where mothers have unintentionally fallen asleep while feeding their child, and the end result has been infant mortality due to accidental smothering.

Lessening the likelihood of suffocation is one of several aspects which render the instant inventive concept different from other products. A number of attempts to ease the breastfeeding process have been made. The Boppy Company, disclosed in U.S. Pat. No. 5,261,134 (1993), is one of the most popular breastfeeding apparatuses on the consumer market. This pillow rests on any solid foundation and helps support the weight of the child during breastfeeding. It also supports the child's head elevation to a degree; however, while this pillow can work well at home, the large and bulky size of this product makes it inconvenient to transport around so it can only be used in a limited area and cannot travel easily outside of the home. Additionally, while using the Boppy, the woman is not able to nurse hands free and may still need to manually hold her breast throughout a feeding. There are multiple devices that are specifically designed to offer a hands-free breastfeeding experience. U.S. Pat. No. 7,059,935 to Jamshidi (2006), U.S. Pat. No. 6,502,262 to Piscopo (2003), and U.S. Pat. No. 6,237,599 to Maulding (2001). Also U.S. patent Ser. No. 09/824,914 by Aranas (2002), Ser. No. 09/824,600 by Schmitter et al. (2001) and Ser. No. 09/873,161 (2007) offer products that are more convenient for travel and compact in size, but the issue with these items is that the designs may not offer sufficient breast support or full consistent coverage as they only cover certain sections of the breast tissue (i.e. top, bottom, or sides). The bulkiness of many of these products, particularly those that are in pillow form, can be a suffocation risk if not properly utilized. These products are more about making the mother's experience easier and more comfortable, as opposed to providing that luxury in addition to preventing the breast from covering a child's nose.

Furthermore, in the aforementioned patents, usage of items such as a pillow or any related invention dealt with making the user experience more comfortable and hands-free, but they lack in terms of offering a form of safety by lessening the likelihood of infant suffocation and/or smothering while nursing by a mother's own breast tissue.

Exemplary embodiments of the present inventive concept seek to overcome some of the above-mentioned deficiencies.

SUMMARY

An aspect of an exemplary embodiment is to provide a breast-size adjustable breastfeeding band which comprises a primary band which is fitted around the middle portion of the breast and compresses the breast tissue substantially by wrapping around the breast. The breastfeeding band also comprises of an adjustable strap attachment which attaches to the primary band to prevent the primary band from sliding on and/or off the breast.

The breastfeeding band is size adjustable, so it stays snug during a feeding while extending around the entire breast, applying enough pressure for secured breast support without being excessive in size or uncomfortable when utilized.

In one exemplary embodiment, the primary band is comprised of a stretchable material, such as elastic, and has first and second ends which allows each end of the primary band to connect together around the breast using a button through one of slits on an elastic band, by a snap button, Velcro, drawstring, and/or hook and eye-type fasteners. The primary band includes a fabric material which is attached to the primary band at the first end and covers approximately 25 percent to 90 percent of the elastic band. At least two metal hooks/bars (or like fastener types) are sewn onto the primary band where one hook is sewn onto the primary band itself and the other on the fabric material.

In another exemplary embodiment, the adjustable strap attachment connects to the primary band via at least one hook and eye-type fastener and it can be tightened behind the neck of a user using a binding apparatus. The adjustable strap attachment is configured of a single strand of material which varies in length and is bound together in the middle of the strand material by a binding apparatus, that is used to shorten or lengthen said single strand, thereby creating two respective strand portions on each side of the binding apparatus. Each of the two respective strand portions include a metal hook which is sewn and/or affixed on each end which can connect and/or hook and/or affix into the primary band to keep the breast-feeding band secured and in place while in use.

The above object, purposes, features, and advantages of the present invention are readily apparent from the enclosed details description of the best mode(s) for carrying out the invention when taken in connection with the accompanying drawings/figures which offer illustrative details of the embodiments.

BRIEF DESCRIPTION OF THE DRAWINGS

Exemplary embodiments of the inventive concept will be more clearly understood from the following detailed description taken in conjunction with the accompanying drawings in which:

FIG. 6 is the perspective of the baby nursing without the primary band or adjustable strap attachment resulting in the covering of the baby's nose; and FIG. 7 is the perspective of the baby nursing with the primary band in place demonstrating the baby's nose exposed and air flowing, according to an exemplary embodiment.

DETAILED DESCRIPTION OF EXEMPLARY EMBODIMENTS

Figure 1:
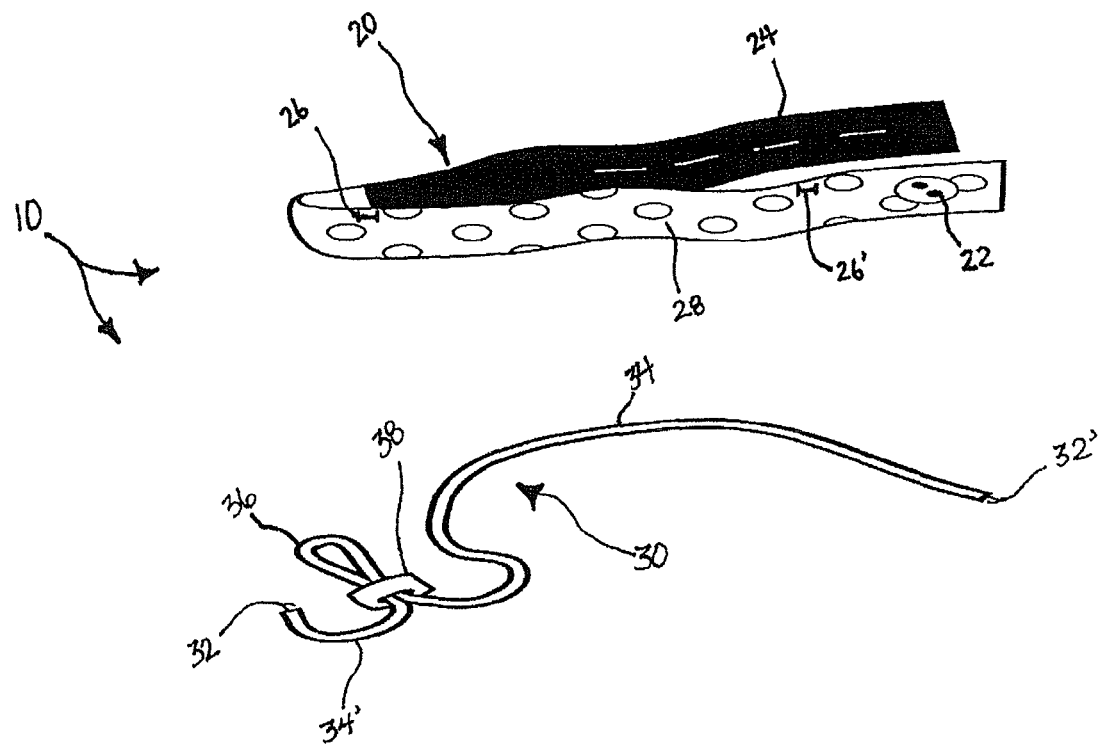
FIG. 1 is a perspective view of the primary band and the adjustable strap attachment having an adjoining or interconnected construction, according to an exemplary embodiment.
Figure 2:
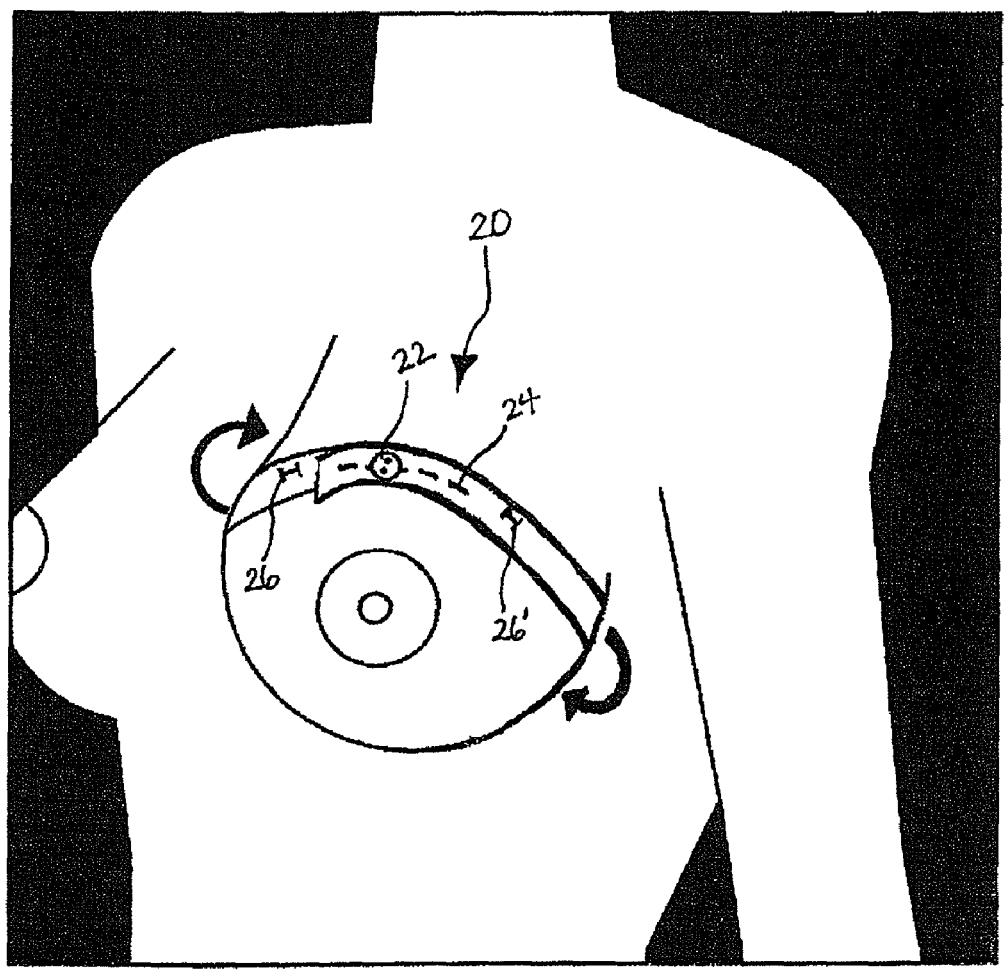
FIG. 2 is a perspective view of the primary band, according to an exemplary embodiment, worn by a female.
Figure 3:
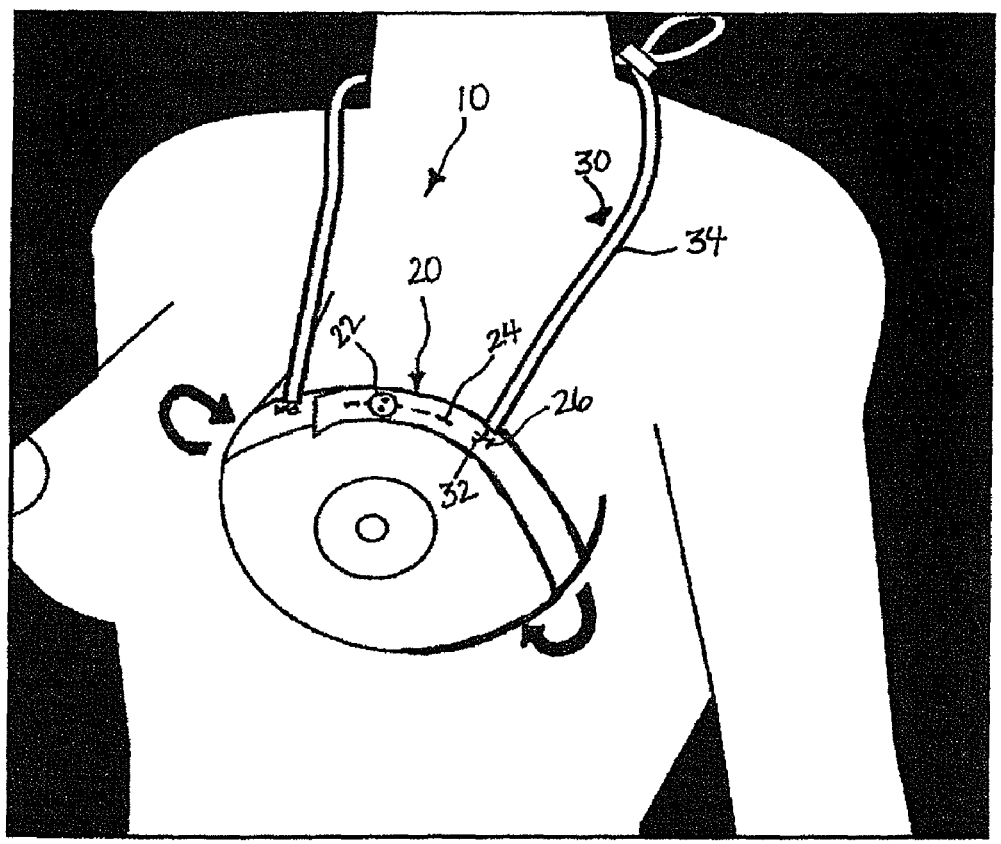
FIG. 3 is a perspective view of the primary band and the adjustable strap, worn by a female, showing an alternate attachment method with the cord plug/clasp behind the neck and both loose-end strands draped over the chest, according to an exemplary embodiment.

Referring to FIGS. 1, 2, and 3, the primary band 20 and adjustable strap attachment 30 are shown as unworn and worn by the user. The breastfeeding band 10 is comprised of the primary band 20 and the adjustable strap attachment 30. Primary band 20 may be made out of elastic or any other stretchable material and its measurements vary, depending on the size of the breast and the structural version used. The typical primary band 20 measurements can vary up to 4 inches wide or more and up to 20 inches long or more. The primary band 20 material can be washable so that it can be cleaned and reused. Primary band 20 can include a soft material covering 28, preferably cotton, but can be any other material that is washable and comfortable for the user. This soft material covering 28 may aid in the comfort of the band around a user's breast while helping to keep the primary band 20 in place during a feeding, in addition to being used to absorb leaking milk. Primary band 20 may have two metal bars 26 (loops or like fasteners) sewn in two spots, several inches apart on either the primary band 20 and/or the soft material covering 28. Primary band 20 may have horizontal slits 24 along the middle of the band. On one end of primary band 20, a button 22 (or any other attachable material—snap, Velcro, drawstring, rope and/or string, adhesive, plastic, etc.) is sewn and/or affixed onto the soft material covering 28.

Figure 4:
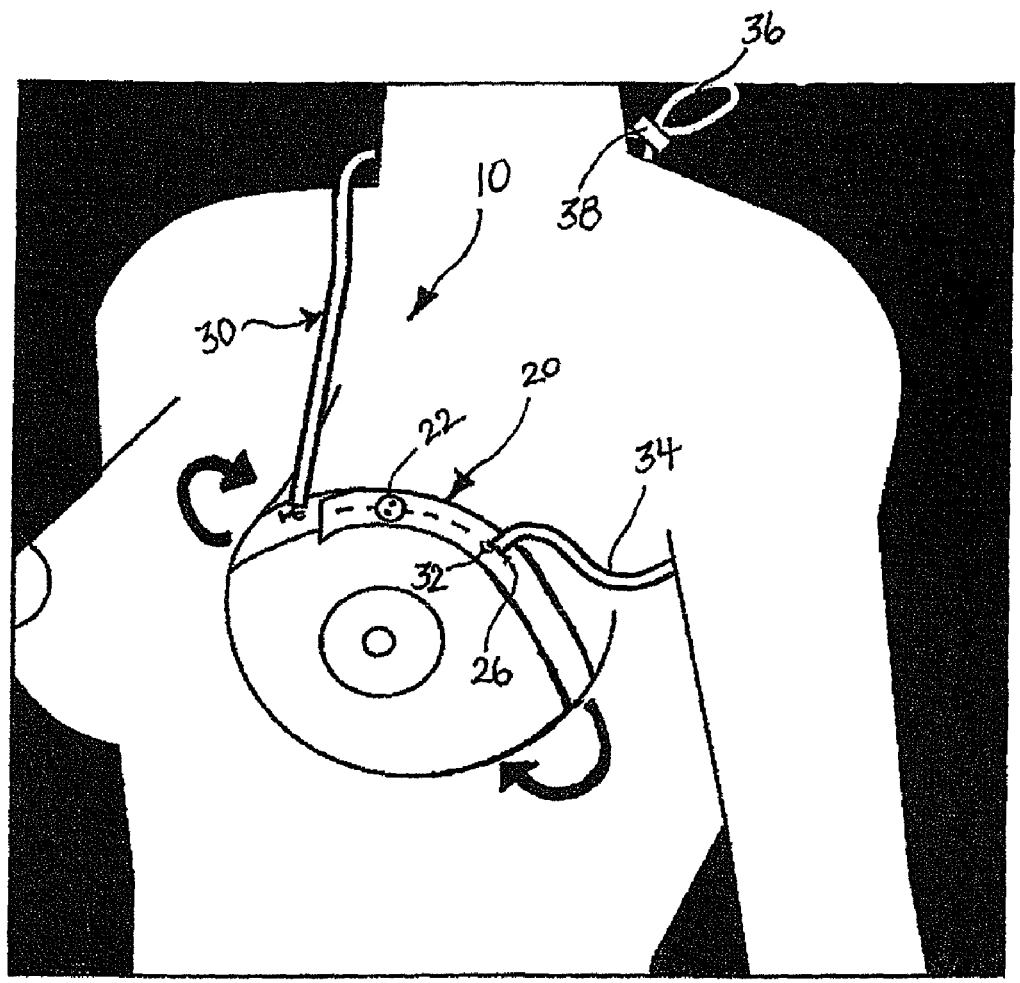
FIG. 4 is a perspective view of the primary band and the adjustable strap, according to an exemplary embodiment, worn by a female, showing an alternate attachment method with the cord plug/clasp behind the neck, one loose-end strand draping over the chest, and the other draped underneath the underarm.

The primary band 20 can be fully utilized on its own as an individual, independent device (as shown in FIGS. 2 and 7); however, for ultimate security and to help prevent the primary band 20 from sliding, there can be an added benefit in that the primary band 20 can attach to the adjustable strap attachment 30 (drawstring appendage, as shown in FIGS. 1, 3 and 4). The benefits of the adjustable strap attachment 30 include that it provides additional security, helping to prevent the primary band 20, when properly tightened around the breast, from shifting and/or sliding off the breast during the nursing process. The adjustable strap attachment 30 may consist of a single strand of durable material (or can comprise of two separate strands of material) that can measure up to 6 ft long or more or less and the middle of the single strand 36 can be gathered/collected by and via a drawstring cord plug/clasp 38 (or like binding apparatus), while the opposite ends of the adjustable strap attachment material dangle as two separate, loose-end strands 34. Each loose-end strand 34 has a hook 32 (or any other plastic, loop, hook or fastener-type device) sewn and/or affixed onto the end.

The adjustable strap attachment 30 can firmly secure primary band 20 in place when hook 32 (or any other plastic, loop, hook or fastener-type device) connects/attaches/fastens into the metal bars 26 (or any other plastic, loop, hook or fastener-type device) on said primary band 20. An exemplary location for metal bars 26 is closer to the top portion and/or along the edge of said primary band 20 (as shown in FIG. 1), but they can be placed in other areas of the primary band 20.

To properly fit a wearer/user, an elastic or other stretchable material which comprises said primary band 20 can be connected by wrapping 365 degrees around the user's breast whereas the primary band 20 connects on one end via button 22 (snap, adhesive, drawstring, Velcro, or like fastener) and the other end via horizontal slits 24. The primary band 20 has diverse options for utilization and may be (1) independently fitted to cinch snugly to and around the breast without causing discomfort (as shown in FIGS. 2 and 7), but tight enough as not to easily slide and to compress breast tissue; (2) attached to the adjustable strap attachment 30 by placing the cord plug/clasp 38 (or like binding apparatus) behind the user's neck with both loose-end strands 34 draping over the chest, with the hooks 32 (or like fasteners) at the end of each loose-end strand and connecting into the metal bars 26 (or like fasteners) on the primary band 20, and being tightened by pulling the loop 36 through the cord plug/clasp 38 (or like binding apparatus) behind the user's neck thus tightening the loose-end strands 34 (as shown in FIG. 3); (3) attached to the adjustable strap attachment 30 by placing the cord plug/clasp 38 (or like binding apparatus) behind the user's neck, with one loose-end strand 34 draping over the chest and the other loose end strand 34' draped underneath the underarm, with the hooks 32 (or like fasteners) at the end of each loose-end strand and connecting into the metal bars 26 (or like fasteners) on the primary band 20, and being tightened by pulling the loop 36 through the cord plug/clasp 38 (or like binding apparatus) behind the user's neck, thus tightening the loose-end strands 34 (as shown in FIG. 4). With each utilization option, the adjustable strap attachment 30 can be adjusted/tightened according to the user's acceptable comfort level via the cord plug/clasp 38 (or like binding apparatus) behind the neck. The above-discussed fittings are only exemplary, and the inventive concept may be implemented via other types of fittings.

As shown in FIGS. 6 and 7, the side view is of the baby nursing without the said breastfeeding band 10 demonstrating the smothering of the baby's nose, and then after when the primary band 20 of the said breastfeeding band 10 is properly placed to cinch around the user's breast, thus holding some of the excess breast tissue away from the baby's nose and opening more of the airflow to the baby's nose. In FIG. 7, the primary band 20 compresses the non-areola/non-nipple portion of the breast above and around the areola/nipple portion keeping the breast tissue down and away from the child's nose. The primary band 20 allows the areola/nipple portion of the breast to protrude forward, thus improving the child's ability to latch onto the mother's breast. A product like this is especially necessary for a mother with larger breasts (but is useful to women of all breast sizes) and can lessen the likelihood of suffocation by breast tissue during the nursing process. The breastfeeding band 10 and each of its structural components can afford a user a hands-free nursing experience as the user does not have to hold the breast tissue away from the child's nose with their hand(s). Instead, they can use their hand to do other things such as read to the baby or perhaps caress their baby.

The soft material covering 28 may be made from any durable and comfortable material and attached to primary band 20 as shown in FIGS. 1 and 7.

Figure 5:
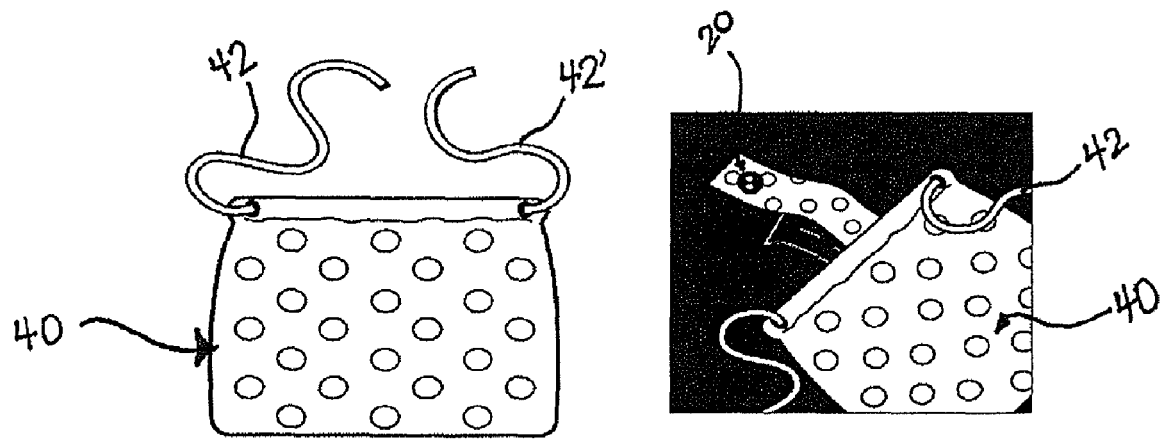
FIG. 5 is the perspective view of the transportable pouch with drawstrings having the ability to store the primary band and the adjustable strap attachment, according to an exemplary embodiment.

Additionally, the primary band 20 and adjustable strap attachment 30 can be conveniently stored inside of the transportable pouch 40 (as seen in FIG. 5) which can be made out of the same or similar fabric as the soft material covering 28. The transportable pouch 40 is opened and closed via drawstring 42 or any other material or method that keeps the primary band 20 and/or adjustable strap attachment 30 from falling out of the transportable pouch 40 (as shown in FIG. 5). For the user's convenience, the transportable drawstring pouch can be stored into a pocket, purse, diaper bag, wrapped around the wrist, etc.

While the inventive concept has been particularly shown and described with reference to exemplary embodiments thereof using specific terms, the embodiments and terms have been used to explain the inventive concept and should not be construed as limiting the scope of the inventive concept defined by the claims. The exemplary embodiments should be considered in a descriptive sense only and not for purposes of limitation. Therefore, the scope of the inventive concept is defined not by the detailed description of the inventive concept but by the appended claims, and all differences within the scope will be construed as being included in the inventive concept

What is claimed is:

1. An adjustable breastfeeding system comprising:
   a primary band which is adapted to compress breast tissue substantially around a portion of only one breast at a time, by wrapping around said only one breast;
   an adjustable strap attachment which attaches to the primary band to at least keep said primary band from sliding on or off the only one breast,
   wherein the primary band and the adjustable strap attachment are separate, and
   wherein the primary band has a first end and a second end that are directly connectable together around the only one breast.

2. The adjustable breastfeeding system of claim 1, wherein the primary band is fitted substantially around a middle portion of the breast.

3. The adjustable breastfeeding system according to claim 1, wherein said adjustable strap attachment is tightenable behind a neck of a user.

4. The adjustable breastfeeding system of claim 1, wherein the primary band is stretchable.

5. The adjustable breastfeeding system of claim 1, wherein said first end and said second end are connected around the breast using a button through one of slits on an elastic band, by a snap, Velcro, drawstring, and/or hook and eye-type fasteners.

6. The adjustable breastfeeding system of claim 1, wherein the primary band includes an elastic band and fabric material which covers approximately 25 percent to 90 percent of the elastic band.

7. The adjustable breastfeeding system of claim 6, wherein at least two metal hooks/bars are sewn onto the primary band, one on the elastic band and one on the fabric material.

8. The adjustable breastfeeding system of claim 1, wherein the adjustable strap attachment connects to the primary band via at least one hook and eye-type fastener.

9. The adjustable breastfeeding system of claim 1, wherein the adjustable strap attachment comprises a single strand and is bound together substantially in a middle of the strand by a binding apparatus, which is used to shorten or lengthen said single strand, thereby creating two respective strand portions on each side of the binding apparatus.

10. The adjustable breastfeeding system of claim 9, wherein each of the two respective strand portions include a metal hook on each end.

11. The adjustable breastfeeding system of claim 6, wherein said fabric material provides a level of comfort to the breast when the primary band is wrapped around the breast.

12. The adjustable breastfeeding system of claim 1, wherein said primary band compressing said breast tissue causes a nipple of said breast to further protrude away from fatty tissue of said breast.

13. A method of breastfeeding, said method comprising:
    providing a primary band;
    said primary band adapted to compress breast tissue by wrapping around only one breast at a time;
    providing and attaching an adjustable strap attachment to said primary band to at least prevent said primary band from sliding on or off said only one breast.

14. The method of breastfeeding according to claim 13, wherein the primary band and the adjustable strap attachment are separate, and wherein the primary band has a first end and a second end that are connectable together.

15. The method of breastfeeding according to claim 13, wherein said adjustable strap attachment is tightenable behind a neck of a user.

16. The method of breastfeeding according to claim 13, wherein the adjustable strap attachment comprises a single strand and is bound together substantially in a middle of the strand by a binding apparatus, which is used to shorten or lengthen said single strand, thereby creating two respective strand portions on each side of the binding apparatus.

17. The method of breastfeeding according to claim 16, wherein each of the two respective strand portions include a metal hook on each end.

* * * * *